United States Patent
Fassihi et al.

(10) Patent No.: US 6,936,275 B2
(45) Date of Patent: *Aug. 30, 2005

(54) AMINO ACID MODULATED EXTENDED RELEASE DOSAGE FORM

(75) Inventors: A. Reza Fassihi, Ambler, PA (US); Thomas Dürig, Chadds Ford, PA (US)

(73) Assignee: Scolr, Inc., Redmond, WA (US)

( * ) Notice: Subject to any disclaimer, the term of this patent is extended or adjusted under 35 U.S.C. 154(b) by 160 days.

This patent is subject to a terminal disclaimer.

(21) Appl. No.: 10/364,793

(22) Filed: Feb. 11, 2003

(65) Prior Publication Data

US 2003/0219480 A1 Nov. 27, 2003

Related U.S. Application Data (63) Continuation-in-part of application No. 09/997,377, filed on Nov. 30, 2001, now Pat. No. 6,517,868, which is a continuation-in-part of application No. 09/467,169, filed on Dec. 20, 1999, now abandoned.

(51) Int. Cl.$^7$ .............................. A61K 9/26; A61K 9/16; A61K 47/00

(52) U.S. Cl. ................. 424/470; 424/464; 424/465; 424/468; 424/469; 424/475; 424/482; 424/484; 424/485; 424/486; 424/488; 424/489; 424/490; 424/499; 424/500; 424/501; 514/769; 514/972; 514/772.3; 514/773; 514/777; 514/778; 514/780; 514/781; 514/782; 514/784; 514/788; 514/960; 514/961; 514/964; 514/965

(58) Field of Search .................... 424/464, 465, 424/468, 469, 470, 475, 477, 478, 479, 480, 481, 482, 484, 485, 486, 488, 489, 490, 499, 500, 501; 514/781, 782, 772, 772.3, 769, 773, 777, 778, 780, 784, 788, 960, 961, 964, 965

(56) References Cited

U.S. PATENT DOCUMENTS

| | | |
|---|---|---|
| 4,675,339 A | 6/1987 | Inoue et al. |
| 4,994,276 A | 2/1991 | Baichwal et al. |
| 5,128,143 A | 7/1992 | Baichwal et al. |
| 5,135,757 A | 8/1992 | Baichwal et al. |
| 5,288,500 A | 2/1994 | Ibsen |
| 5,292,518 A | 3/1994 | Kuhrts |
| 5,393,765 A | 2/1995 | Infeld et al. |
| 5,455,046 A | 10/1995 | Baichwal |
| 5,697,922 A | 12/1997 | Thombre |
| 5,811,388 A | 9/1998 | Friend et al. |
| 5,874,106 A | 2/1999 | Adesunloye et al. |
| 6,517,868 B2 * | 2/2003 | Fassihi et al. .............. 424/470 |

FOREIGN PATENT DOCUMENTS

EP  WO 99/21551  5/1999

OTHER PUBLICATIONS

Altaf et al. "Guar Gum–Based Sustained Release Diltiazem" *Pharmaceutical Research*, vol. 15, pp. 1196–1201 (1998).

Yu et al. "Guar Gum" pp. 245–277 (1998).

Database BIOSIS on STN/CAS. Acc. No. 1991:162706, DN BA91:88506. Solubilization effects of L Proline on slightly water–soluble drugs. Watanabe et al., 1990. vol. 50. No. 4, pp. 397–401, Abstract.

Database CAPLUS on STN/CAS, Acc. No. 1978:412044, DN. 89:12044. The effect on the water solubility of several drugs by electrolytes. Part 4. Amino acids. ROHDEWALD, 1978, vol. 123, No. 9, pp. 371–375, Abstract.

International Search Report dated May 31, 2002.

* cited by examiner

*Primary Examiner*—S. Mark Clardy
*Assistant Examiner*—Frank Choi
(74) *Attorney, Agent, or Firm*—RatnerPrestia

(57) ABSTRACT

Disclosed herein is a oral extended release dosage form comprising a plurality of granules of an effective amount of a pharmaceutically active compound, at least one amino acid, and an intragranular polymer in which the granule is dispersed within a hydrophilic extragranular polymer matrix which is more rapidly hydrating than the intragranular polymer. The amino acid is selected for hydropathy characteristics depending on solubility characteristics of the active compound.

26 Claims, 5 Drawing Sheets

FIG. 1A

EFFECT OF AMINO ACID ON A TYPICAL VERAPAMIL FORMULATION CONTAINING GUAR AS INTRA- AND EXTRAGRANULAR POLYMER

FIG. 1B

EFFECT OF AMINO ACID ON A TYPICAL DRY BLENDED, NON-GRANULATED VERAPAMIL FORMULATION

FIG. 2A

EFFECT OF A COMBINATION OF ISO-LEUCINE AND GLYCINE ON A GRANULATED NIFEDIPINE FORMULATION (AS AN EXAMPLE OF AN INSOLUBLE DRUG)

FIG. 2B

EFFECT OF A COMBINATION OF ISO-LEUCINE AND GLYCINE ON A DRY BLENDED, NON-GRANULATED NIFEDIPINE FORMULATION

FIG. 5

AMINO ACID MODULATED EXTENDED RELEASE DOSAGE FORM

The present application is a continuation-in-part of U.S. patent application Ser. No. 09/997,377, filed Nov. 30, 2001 now U.S. Pat. No. 6,517,868, which is a continuation-in-part of U.S. patent application Ser. No. 09/467,169, filed Dec. 20, 1999 now aband., the entire contents of each of which are hereby incorporated herein by reference.

FIELD OF THE INVENTION

The present invention is directed to an oral tablet containing pharmaceutically active compounds. The present invention finds particular usefulness in producing controlled drug release and ease of tablet manufacture. In particular, the invention is directed to drug tablets having minimal "burst effect" and a more linear drug release profile over an extended period of time.

BACKGROUND OF THE INVENTION

In traditional sustained release matrix systems, the drug is incorporated into a matrix consisting of either hydrophobic or hydrophilic materials such as polymers. The predominant mechanism of drug release from such systems is diffusion, resulting in curved release profiles that can be described by square root of time kinetics. Such release profiles are characterized by initial rapid release followed by a gradual decline in the rate of release, resulting in a prolonged "tailing off" in the late time phase. This "tailing off" is often accompanied by incomplete dissolution. Furthermore, there is typically an initial rapid release described as a "burst effect" which is attributed to the initial rapid wetting and dissolution of drug on the surface of the dosage form. This type of curved release profile may be a disadvantage for drugs that are to be absorbed throughout the gastrointestinal tract over an extended period of time at a controlled or constant rate. More specifically, the amount of drug available for absorption, over a period of drug release, steadily decreases. This may necessitate more frequent dosing compared to a dosage form that has a more linear drug release profile over an extended period of time. However, even in formulations that have a near zero order release, burst effects are frequently seen. The burst effect can be expected to be especially problematic as drug load increases, because by implication the concentration of drug at the tablet surfaces increases.

A number of approaches have been adopted to counteract the natural diffusive processes which control mass transfer from compressed tablets into surrounding aqueous dissolution media and to limit the burst effect. In particular, several methods to achieve so-called "zero order" controlled release or constant rates of release and approximate linear release profiles have been developed. These approaches include geometric modifications of the tablet, resulting in control of the surface area available for drug diffusion. Other examples include the use of multiple layer tablets, osmotic pumps, and coated pie shaped and hemispherical tablets with strategically located un-coated portions of surface area.

Many of the above named systems are of great utility, however they suffer shortcomings in that they are relatively costly and complicated to manufacture, often requiring multiple manufacturing steps and specialized equipment.

In addition, osmotic pump systems and multiple layer systems tend to deliver the drug in linear fashion only to about 85% of the total drug loaded, with severe tailing off thereafter. In the case of oral osmotic systems, this effect may be ascribed to the exhaustion of the reservoir device and the loss of osmotic pressure. Also, the aforementioned devices are of limited usefulness for the controlled delivery of large doses of medicament, for example more than 600 mg., especially if the medicament is relatively water soluble. In such cases of high drug loading, the addition of an absolute minimum of rate controlling excipient is necessary to achieve a tablet size that can be comfortably swallowed. Additionally, the need to add relatively large amounts of osmoagent and/or hydrophilic rate controlling swelling polymer layers severely limits the maximum drug load achievable in such systems.

Thus there is a need for a simple monolithic matrix tablet that is capable of delivering a high drug load irrespective of drug solubility to approximate zero order release kinetics.

In recent years, the value of hydrophilic polymer based systems employing controlled release has been increasingly demonstrated with the publication of numerous patents and research papers. Infield et al., U.S. Pat. No. 5,393,765, describes a hydrophilic erodible monolithic tablet formulation capable of approximating zero order drug release based on hydroxypropylmethyl cellulose and various erosion enhancing excipients such as lactose and surfactants such as Pluronic®. These constituents are mixed with a drug to form a matrix, and subsequently tableted. When ingested, the Infield et al. matrix forms two layers, an outer layer of hydrated matrix and an inner layer of unchanged matrix.

While semi-synthetic cellulose derivatives have found wide use in controlled release formulations, a number of polysaccharide based excipients have also been employed in oral controlled release systems. Polysaccharides which have been used as controlled release excipients, and have been employed on their own or in combination with other excipients, include chitosan, alginic acid, carrageenan, scleroglucan, and modified starch products.

Xanthan gum, a semi-synthetic polysaccharide of bacterial origin, has also received frequent attention as a controlled release material. The potential of xanthan gum alone has been evaluated, and a number of studies of xanthan gum in combination with alginic acid or guar gum have also been published. Baichwal et al., U.S. Pat. Nos. 4,994,276, 5,128,143, and Staniforth et al., U.S. Pat. No. 5,135,757, disclose controlled release excipient systems utilizing xanthan gum and a synergistically interacting polysaccharide such as locust bean gum or guar gum, along with secondary and tertiary components such as saccharides or other hydrophilic polymers. In these patents, it is speculated that a synergistic interaction occurs between xanthan and the polysaccharide gum resulting in an increased viscosity and gel strength. Based on similar principles of a synergistic interaction between xanthan and a gum, Baichwal, et al., U.S. Pat. No. 5,455,046, discloses a sustained release dosage form suitable for insoluble drugs such as nifedipine by employing cross-linked heteropolysaccharides and polysaccharides.

Guar, a natural galactomannan, obtained from the seeds of *Cyanopsis tetragonolobus* has found use in the pharmaceutical industry as a disintegrating and binding agent for tablets, as well as a suspending, thickening, and stabilizing agent for liquid and semi solid products. Guar gum has also been used in some extended release formulations and combinations of xanthan gum and guar gum have been extensively studied. The studies indicate that in certain instances, large amounts of hydroxypropylmethyl cellulose had to be added to guar gum to achieve acceptable sustained release formulations. Altaf et al. (1998) and Yu et al. (1998) published articles on a guar gum based sustained release formulation containing diltiazem which was shown to be equivalent in vitro and in vivo to a commercial product (Dilacor XR®). However, neither of these two preparations achieved a predominantly zero order release profile. Khurts, in U.S. Pat. No. 5,292,518, discloses prolonged release formulations consisting of gel forming dietary fiber, such as guar gum, a drug, a mineral salt, which releases a physiologically acceptable gas on ingestion, disintegrants and binders. Optionally, organic acids such as maleic and citric acid can be included to further aid disintegration.

Furthermore, guar gum has been found to undergo efficient enzymatic degradation in the human large intestine and has therefore been used as a carrier for colon specific drug delivery. Modifying guar gum with borax or glutaraldehyde has been reported as an effective means of producing cross linked polymers with limited swelling potential and increased viscosity. The limited swelling and increased viscosity reportedly increases the potential for the polymer matrix to stay intact and release a minimum of drug until the colon is reached. Friend and Wong, U.S. Pat. No. 5,811,388, disclose a simple formulation consisting of a drug useful for treating colonic disorders or a peptide drug that can be absorbed from the colon, and a hydrocolloid gum obtainable from higher plants, preferably guar gum. The authors mention the possible inclusion of a host of substances that may serve to stabilize a peptide or protein drug, or aid in drug penetration of gastrointestinal membranes and absorption.

Amino acids such as glycine find frequent use as plasticizers in polymer film coatings, as buffering agents and excipients used in the stabilization and formulation of lyophilized products, injectables, nose drops and oral solutions. For example, DL-leucine has been used as a hydrophilic lubricant. Ibsen, U.S. Pat. No. 5,288,500, discloses the possible use of amino acids in combination with hydrophilic polymers to enhance rapid swelling in order to mask grittiness and taste in formulations of granules that are to be rapidly dispersed in water prior to ingestion. Adesunloye, U.S. Pat. No. 5,874,106, discloses that amino acids in combination with carboxylic acids such as citric acid, prevent cross-linking in gelatin capsules. Finally, Thombre et al., U.S. Pat. No. 5,697,922, describe an osmotic device wherein solubility adjusting substances, which may simultaneously act as osmoagents, can be made into coated macro particles. These solubility adjusting substances may include ionizing substances, salts, surfactants or amino acids.

Though useful as dosage forms, the release profiles of many of the prior compositions are usually characterized by initial rapid release followed by a gradual decline in the rate of release, resulting in a "prolonged tailing off" in the late time phase. The "tailing off" often results in incomplete dissolution and failure to achieve 100% drug release. Furthermore, there is typically an initial "burst effect", causing a relatively large amount of drug to be released early in dissolution, which is attributed to the initial rapid wetting and dissolution of drug on the surface of the dosage form. Lastly, many such systems suffer practical shortcomings in that they are relatively costly and complicated to manufacture, often requiring multiple manufacturing steps and specialized equipment.

Kim et al., WO 99/21551, discloses a simple polymeric matrix tablet that is designed to deliver drugs over extended periods of time, while being relatively easy to manufacture. The drug is first granulated with a swellable polymer to form granules. The granules are then dispersed within a matrix of a more swellable, erodible polymer and compressed to form a monolithic matrix tablet which is readily manufactured on commercial high speed tabletting equipment. Kim et al. does not make use of amino acids to mediate polymer swelling and dissolution of the drug, and the solubility of the drug plays the greatest role in determining the release profile and release duration. Therefore, Kim et al. is limited in application to highly soluble drugs.

The present invention provides an extended release dosage form for simple monolithic matrix tablets capable of delivering a high drug load of pharmaceutically active substances according to zero order release kinetics over an extended period of time, preferably 12 to 24 hours, in which drug release is mediated by the inclusion of an amino acid.

Definitions

As used herein the following terms have the definitions set forth below.

"Hydropathy" refers to a scale of solubility characteristics combining hydrophobicity and hydrophilicity of amino acids. More particularly this term refers to a sliding scale, similar to a pH scale, which assigns relative values which represent the relative balance between hydrophobic and hydrophilic components of an amino acid. A typical scale is set forth in Pliska et al., J. Chromatog. 216, 79, 1981, entitled Relative Hydrophobic Character of Amino Acid Side Chains, wherein glycine has a value of 0, representing a relatively equal balance between hydrophobic and hydrophilic components and may be referred to as relatively 'neutral', 'balanced', 'slightly hydrophilic'; or 'weakly hydrophobic', iso-leucine has a positive value of 1.83 and is strongly hydrophobic, and on the opposite end of the scale, aspartic acid has a negative value of −2.15 and may be characterized as strongly hydrophilic. Such a scale and the hydropathy characteristics described herein are well known and understood by those skilled in the art. Representative values and hydropathy characteristics are set forth in Table 1.

"Monolithic" refers to tablets that do not require multiple layers, special shapes, osmotic compartments and/or specialized coatings, typically without joints or seams, and are capable of being tableted on modern high speed tableting equipment.

SUMMARY OF THE INVENTION

The present invention provides an oral extended release dosage form comprising a plurality of granules of a pharmaceutically active compound granulated with at least one amino acid and an intragranular polymer. The granules are dispersed within a hydrophilic extragranular polymer to form a monolithic matrix. The extragranular polymer is more rapidly hydrating than the intragranular polymer in order to approximate 100% release of the active compound while maintaining a linear release profile and minimizing the complication and cost of manufacture of compressed monolithic tablets. The amino acid is selected for hydropathy characteristics which depend on the solubility characteristics of the active compound.

This invention also comprises a process for making a tableted oral extended release dosage form comprising mixing a pharmaceutically active compound with an intragranular polymer and at least one amino acid; granulating the mixture to form granules; blending the resulting granules with a more rapidly hydrating extragranular polymer to disperse the granules within the matrix of extragranular polymer, and compressing the resulting blend to form a simple monolithic tablet which approximates zero order release of the pharmaceutically active agent over an extended period of time.

In its simplest form, the present invention is a pharmaceutically active agent combined with an intragranular polymer and at least one amino acid and granulated by any suitable means to form granules. The granules are then blended with and dispersed within an extragranular polymer. The granulation may then be compressed to form an extended release monolithic matrix tablet.

DETAILED DESCRIPTION OF THE INVENTION

The present invention provides a formulation for the controlled release of drugs from a monolithic tablet. The oral extended release dosage form comprises a plurality of granules of a pharmaceutically active compound, granulated with at least one amino acid, and an intragranular polymer. The granules are then dispersed within a hydrophilic extragranular polymer. An important aspect of this invention is the use of an extragranular polymer which more rapidly hydrates relative to the intragranular polymer. The rapid hydration of the extragranular polymer assists in the approximation of a linear release profile of the drug and facilitates near 100% dissolution, while extending the duration of release and reducing the burst effect frequently encountered with extended release dosage forms. Although the linear release rate can be tailored to fit the needs of each application by selecting polymers for different dissolution rates, as understood by one of ordinary skill in the art, a release time of 12 to 24 hours is most preferred.

The intragranular polymer is combined with a pharmaceutically active compound, and at least one amino acid to form granules. The intragranular polymer may be one or more of the following: polyethylene oxide, polyvinyl acetate, a galactomannan polysaccharide such as hydroxypropyl guar, guar gum, locust bean gum, pectin, gum acacia, gum tragacanth, karaya gum, cellulose ethers such as hydroxyproplymethyl cellulose (HPMC), as well as other gums and cellulose ethers to be chosen by one of skill in the art for properties consistent with the teaching of this invention. The intragranular polymer is preferably a galactomannan polysaccharide, most preferably guar gum (with a viscosity range of 75–6000 cps for a 1% solution at 25° C. in water and a particle size 10–300 $\mu$m).

The intragranular polymer in the tablet is preferably present in amounts between 4% and 45% of the total dosage form weight. The specific type of intragranular polymer and amount of intragranular polymer used is chosen depending on the desired rate of drug release, viscosity of the polymer, the desired drug load, and the drug solubility. It is an important aspect of this invention that the intragranular polymer hydrates less rapidly than the extragranular polymer. The relative difference in hydration rates between the two polymers creates a less viscous intragranular polymer and a more viscous extragranular polymer. Over time, the difference in viscosity contributes to the continuous erosion and disintegration of the tablet.

Amino acids are useful in this invention for two primary reasons. First, the amino acids are a factor in determining the viscosity of the polymers. As noted above, over time the difference in viscosity between the extragranular and intragranular polymers contributes to the continuous erosion and disintegration of the core, facilitating about 100% release of the drug. Another important aspect of using an amino acid in the granule is that the hydropathy of the amino acid may be exploited to modulate the solubility and release of a drug.

Figure 1A:
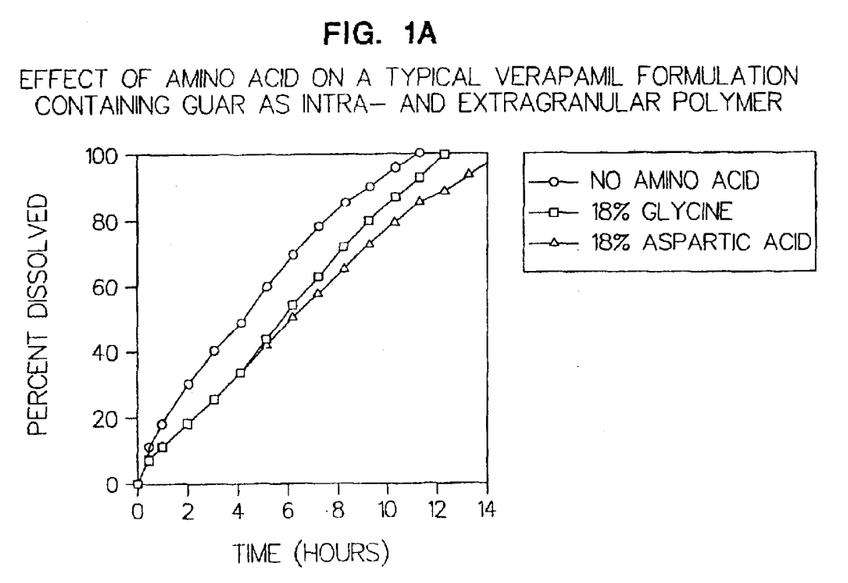
FIGS 1a and 1b illustrate the effects of amino acids on dissolution rates of verapamil HCl formulations.

Thus, the amino acid is selected for hydropathy characteristics depending on the solubility characteristics of the active compound. When the compound is at least sparingly water soluble, that is, for example, sparingly soluble, soluble or has a higher level of solubility, as defined by the United States Pharmacopeia, an amino acid is utilized which has a relatively equal balance between hydrophilic and hydrophobic components, i.e. is neutral or balanced or within close proximity to neutrality, or is relatively more strongly hydrophilic. Typical active ingredients of this type include, for example, verapamil, dimenhydrinate, metformin and pharmaceutically acceptable salts thereof, and other compounds having similar solubility characteristics, which may be used alone or in combination or granulated separately to provide an independent release profile in a single dosage unit, such as a tableted dosage form For example, dissolution and release of soluble or sparingly soluble ionizable drugs such as can be controlled by the inclusion of one or more amino acids in the granules (FIG. 1a). Without subscribing to a particular theory of drug release and dissolution, it is believed that the nature of the granulation process is such that as the formulation components come into close molecular contact, granulation reduces the available surface area of the particles, thus reducing the initial rate of hydration. In the granulated formulations, there is sufficient time for the amino acid carboxyl (COOH-) groups and amino groups ($NH_2/NH_{3+}$) to interact with hydroxyl groups on the polymer, thus mediating the swelling, viscosity, and gel properties of the polymer and thereby exerting control on the swelling mediated drug diffusion. Simultaneously, the amino acid carboxyl groups may also interact with suitable polar substituents on the drug molecule such as secondary or tertiary amines. Furthermore, the hydrophilic and ionic nature of amino acids results in their extensive hydration in aqueous solution. Consequently, the amino acid promotes erosion, but also competes with both the polymer and the drug for water uptake necessary for hydration and dissolution.

However, when the active compound is less than sparingly soluble, including active compounds which are slightly soluble to insoluble, a combination of at least two amino acids is utilized, one of which is strongly hydrophobic, the other of which is relatively more hydrophilic than the hydrophobic component, that is, about neutral or balanced to strongly hydrophilic. Typical active ingredients of this type include, for example, nifedipine, ondansetron, glipazide, paclitaxil and pharmaceutically effective salts thereof, and other compounds having similar solubility characteristics, which may be used alone or in combination or granulated separately to provide an independent release profile in a single dosage unit, such as a tableted dosage form.

Figure 2A:
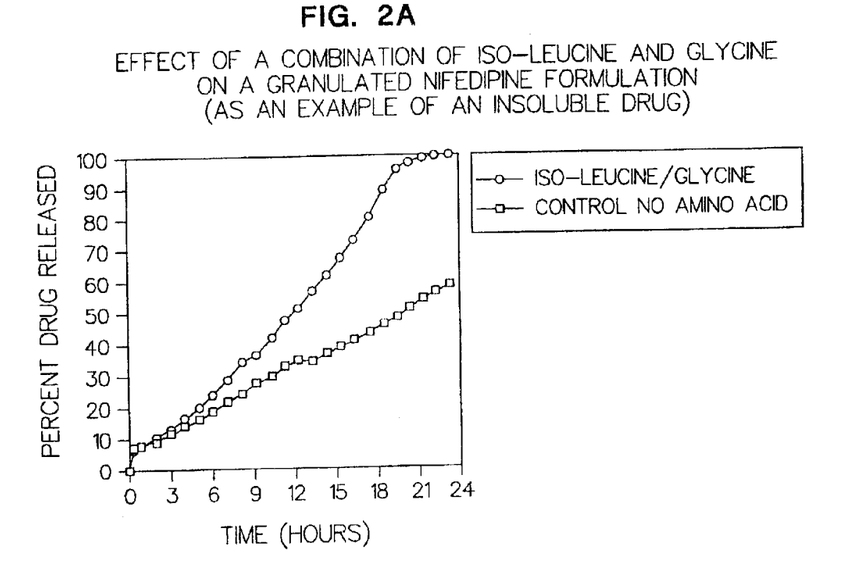
FIGS. 2a and 2b illustrate the effects of amino acids on dissolution rates of nifedipine formulations.
Figure 2B:
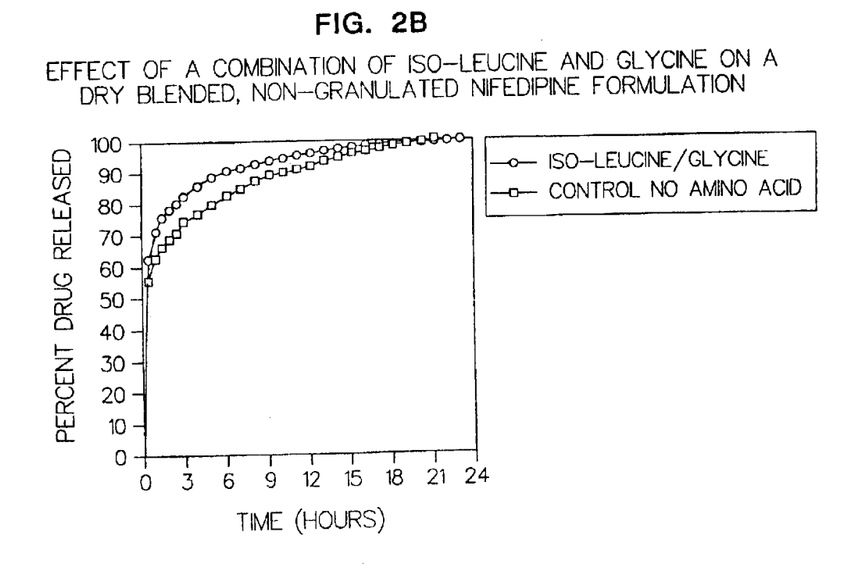

For example, the effect of a combination of amino acids in the intragranular polymer is further illustrated by the example of nifedipine (a water insoluble drug) in FIG. 2(b). The figures illustrate that a particularly beneficial composition can be achieved by granulating (1) nifedipine, (2) a hydrophobic amino acid, for example iso-leucine or phenylalanine, and (3) a weakly hydrophobic or hydrophilic amino acid, such as glycine, in which there the hydrophobic and hydrophilic components are relatively equal or balanced, and guar. The combination results in a marked increase in the dissolution rate of nifedipine, thus allowing complete (near 100% of dose) dissolution in an approximately linear fashion. Without subscribing to a particular model of drug dissolution, it is believed that the above composition facilitates the close molecular association and possible weak complexation between the hydrophobic side chain of a strongly hydrophobic amino acid such as iso-leucine and the strongly hydrophobic nifedipine molecules. Simultaneously, the less hydrophobic glycine molecules are effectively able to intersperse themselves between, and able to interact with, the polar portions of the iso-leucine molecules. When exposed to water, the rapidly dissolving, more hydrophilic glycine molecules "drag" with them, and increase the hydration of, the more hydrophobic iso-leucine molecules which are complexed with nifedipine molecules by hydrophobic interaction.

Further, a pharmaceutically active compound having higher water solubility characteristics, may be combined in a single dosage unit with a compound having lower water solubility by separately granulating each of the active ingredients with an amino acid suitable for that active ingredient as described above, then blending and dispersing the granules into the extragranular polymer.

The amino acid component of the granules may comprise any pharmaceutically acceptable α-amino or β-amino acids, salts of α- or β-amino acids, or any combination thereof. Examples of suitable α-amino acids are glycine, alanine, valine, leucine, iso-leucine, phenylalanine, proline, aspartic acid, glutamic acid, lysine, arginine, histidine, serine, threonine, cysteine, asparagine, and glutamine. An example of a β-amino acid is β-alanine.

The type of amino acids used in the present invention alternatively can be described as hydrophilic, hydrophobic, salts of hydrophillic or hydrophobic amino acids, or any combination thereof. Preferred hydrophobic amino acids for use in the present invention are iso-leucine, phenylalanine, leucine, and valine. Further, hydrophilic amino acids, such as glycine, aspartate and glutamate can be used in the granule. Ultimately, any amino acid, and any amino acid in combination with another amino acid, can be employed in the present invention to enhance the solubility of a drug. For a detailed list of amino acids that can be used in the present invention and the hydropathy of each, see Albert L. Lehninger et al., *Principles of Biochemistry* 113 ($2^{nd}$ ed. Worth Publishers 1993).

The type and amount of amino acid may be chosen depending on the desired drug load, desired rate of drug release, and the solubility of the drug. The amino acid in the dosage form is typically between 4% and 45% of the total dosage form weight. However, the amount of amino acid is preferably between 11% and 29% by weight of the total dosage form.

The granules may optionally be blended with a coating material, for example magnesium stearate or other hydrophobic derivatives of stearic acid. The amount of coating material used can vary from 1% to 3% of the total weight of the dosage form. Normally, magnesium stearate is used to facilitate processing, for example as a flow aid, but in the present invention magnesium stearate has the additional benefit of retarding dissolution, due to the hydrophobic nature of the coating material. Therefore, magnesium stearate can be used to further adjust the solubility of the dosage form and further retard drug release from the granules.

To enhance the mechanical properties and/or to influence the drug release rate further, the granules may also contain small amounts of inert pharmaceutical fillers and binders/granulating agents as is conventional to the art. Examples of inert pharmaceutical fillers include: lactose, sucrose, maltose, maltodextrins, dextrins, starch, microcrystalline cellulose, fructose, sorbitol, di-and tri-calcium phosphate. Examples of granulating agents/binders include starch, methylcellulose, hydroxy propyl- or hydroxypropylmethyl cellulose, sodium carboxymethyl cellulose, or polyvinyl pyrrolidone, gum acacia tragacanth and sucrose. Other suitable fillers may also be employed as understood by one of skill in the art. Depending on the physical and/or chemical properties of the drug, a wet granulation procedure (using either an aqueous or organic granulating fluid) or a dry granulation procedure (e.g. slugging or roller compaction) can be employed.

After the granulation of the pharmaceutically active compound, intragranular polymer, amino acids, and optionally fillers and hydrophobic coating materials, the granule is then blended with and dispersed within an extragranular polymer.

The extragranular polymer may be one or more of the following: polyethylene oxide, a galactomannan polysaccharide such as hydroxypropyl guar, guar gum, locust bean gum, pectin, gum acacia, gum tragacanth, karaya gum, cellulose ethers such as hydroxypropylmethyl cellulose (HPMC), as well as other gums and cellulose ethers to be chosen by one of skill in the art for properties consistent with the teaching of this invention. The extragranular polymer is preferably a galactomannan polysaccharide, most preferably guar gum (with a viscosity range of 75–6000 cps for a 1% solution at 25° C. in water and a particle size 10–300 $\mu$m). As noted above, it is important that the extragranular polymer hydrates rapidly and achieves a high level of viscosity in a shorter period of time relative to the intragranular polymer.

The difference in hydration rates between the extragranular polymer and intragranular polymer is achieved by three principle means, (1) by choosing polymers based on differences in particle size, (2) by choosing polymers based on differences in molecular weight and chemical composition and (3) by choosing polymers based on a combination of (1) and (2). Although this disclosure focuses primarily on polymers chosen for differences in particle size, it is possible to achieve the results of this invention by using an intragranular polymer with a different molecular weight and/or chemical composition than the extragranular polymer. For example, polyethylene oxide may be used as the intragranular polymer and guar gum as the extragranular polymer.

Particle size is an important characteristic of commercial guar gum because coarser particles ensure rapid dispersion, while finer particles are ideal for fast hydration. Therefore, in order to achieve the desired result of the present invention, the finer particles are used for the extragranular polymer and less fine particles are used for the intragranular polymer particles. The brochure by HERCULES Incorporated, entitled "Supercol® Guar Gum, 1997" contains the typical properties of guar gum of different grades and particles sizes. The information in the brochure is readily obtainable to one of ordinary skill in the art and a chart showing the different characteristics of guar gum is included here for completeness:

| Grade of Supercol | Form | Mesh | Viscosity | Rate | Peak Viscosity % in 15 min.* | Dispersibility |
|---|---|---|---|---|---|---|
| G3-S | Coarse | 60 | 4,000 | Slow | 40 | Excellent |
| G2-S | Medium Coarse | 80 | 4,500 | Moderate | 50 | Excellent |
| GF | Medium Fine | 150 | 4,500 | Fast | 70 | Very good |
| U | Fine | 200 | 5,100 | Very Fast | 90 | Fair (requires care) |
| US | Fine | 200 | 5,500 | Very Fast | 90 | Fair (requires care) |
| K-1 | Medium Fine | 150 | 1,200 | Slow | 30 | Fair (requires care) |

*the viscosity was measured at 25° C. after 2 hours, using a Brookfield RVT viscometer at 20 rpm and reported on an as-is basis.

For example, Guar U achieves 90% of its maximum viscosity (5100 cps) in 15 minutes. It is therefore possible to use Guar U as the rapidly hydrating extragranular polymer and Guar G3, which achieves 40% of peak viscosity (4000 cps) in 15 minutes, as the less rapidly hydrating and less viscous intragranular polymer. Other rapidly hydrating extragranular polymers which may be used include: polyethylene oxide (PEO), cellulose ethers and polysaccharides such as hydroxypropyl guar, pectin, gum acacia and tragacanth, karaya gum, mixtures of the aforementioned polymers and any other polymers to be chosen by one of skill in the art for properties consistent with the teaching of this invention. The amounts and the types of extragranular polymer are chosen depending on the desired drug load, rate of drug release and drug solubility. A range of about 4–47% (by total tablet weight) of extragranular polymer has been found to be feasible, but a range of about 15%–47% is particularly preferred.

The present invention is capable of containing a therapeutic amount of a pharmaceutically active compound, preferably up to about 75% of the total dosage form weight. With this drug load, the tableted oral extended release dosage form approximates a linear release profile, with a minimal, or elimination of, burst effect. However, if desired by a skilled artisan, the extragranular polymer may contain additional amounts of the pharmaceutically active compound to achieve more rapid drug release or an induced burst effect, as well as contain amino acids to mediate dissolution of the pharmaceutically active compound, as described above.

The tableted oral extended release dosage form optionally may be coated with polymers, plasticizers, opacifiers, and colourants as is conventional in the art.

The tableted oral extended release dosage form of the present invention is typically prepared as follows.

Appropriate amounts of intragranular polymer, pharmaceutically active compound, and amino acids are weighed. After weighing, each ingredient may optionally be passed through a mesh screen to deagglomerate the constituents into fine powders. Preferably, a #30 mesh screen is used.

The powders are then mixed in a mixer, suitably in a twin shell V-mixer (Patterson-Kelly, East Stroudsburg, Pa.) until the components are evenly mixed, typically about 20 minutes. Optionally, inert fillers may be added during the mixing step.

The mixture is then added to the mixing bowl of a planetary mixer. A granulating fluid such as water, iso-propanol, a mixture of water and iso-propanol, or a pharmaceutically acceptable solvent is added where necessary. The granulating fluid is added while continuously mixing until a coherent wet mass is formed. Typically, coherent wet mass formation takes about 10 minutes. Preferably, the wet mass is hydrated for an additional 15 minutes while constantly stirring.

The wet mass is then passed through a sieve, typically a 1 mm stainless steel sieve, to form granules. The sieve is typically mounted on an oscillating granulator, such as a granulator from Erweka, Heusenstamm, Germany.

Alternatively, granulation may be achieved by a dry granulation process, for example slugging or roller compaction.

The granules are then dried. Typically, the granules are dried on trays, for example in a vacuum oven at 50° C. for about 3.5 hours or until the loss on drying is less than 1.5% of the granule weight.

An amount of extragranular polymer is then added to the granules. Typically, sufficient extragranular polymer is added to achieve an amount of about 4% to about 47% of the total final tablet weight. Preferably, sufficient amounts are added to achieve about 15% to about 47% of the total final tablet weight.

The extragranular polymer and granules are then blended, typically in a twin shell V-mixer, preferably for at least 15 minutes. A small amount (about 0.5% to about 1%) of a lubricant, typically magnesium stearate, may optionally be added to the mixture. This may be accomplished by sieving the lubricant through a fine screen or other methods as is apparent to one of skill in the art.

Prior to compression, additional amounts of lubricant may optionally be added. This is done to induce greater hydrophobicity in the tablet. Typical levels added may be about 1% to about 3% of the total tablet weight.

Also, a flow-promoting agent such as 1–2% talc or colloidal silicon dioxide can be added to the mixture immediately before adding the lubricant. These agents ensure the optimal flow of the powder mixture from the hopper, into the feeding mechanism and die cavities of the tablet press. Uniform fast flow under gravity is essential to ensure uniform filling of die cavities and by implication uniform tablet weights and dosages. However, the granules of the present invention typically have adequate flow properties, thus obviating this commonly used industry practice.

The final mix is suitable for compression on a commercial large scale tablet press. Preferably, compression may be done on a rotary press, such as the Stokes B2 rotary press, or on smaller lab scale presses such as Mannesty F3-single punch press and the Carver manually operated hydraulic press. The settings on the press should be set such that compaction pressure should be in the range of about 160–180 MPa. This yields tablets with hardness of about 70–100 N.

While this invention has been described with reference to specific embodiments, it is not necessarily limited thereto. Accordingly, the appended claims should be construed to encompass not only those forms and embodiments of the invention specifically described above, but to such other forms and embodiments as may be devised by those skilled in the art without departing from its true spirit and scope.

EXAMPLES AND TABLE

The formulations described below have been prepared in accordance with the general procedures described above. In these formulations, an * indicates that a component has been added by dry blending, i.e. it is present as an extragranular excipient.

Example 1

Example 1a (FIG. 1a) illustrates the effect of adding an intragranular amino acid to a typical verapamil formulation containing guar as an intragranular and extragranular polymer.

| Component | Control Formulation | With Glycine | With Aspartate |
|---|---|---|---|
| Verapamil HCl | 120 mg | 120 mg | 120 mg |
| Glycine | — | 54 mg | — |
| Aspartic acid | — | — | 54 mg |
| Guar Gum (G) | 54 mg | 54 mg | 54 mg |
| Guar Gum (U)* | 72 mg* | 72 mg* | 72 mg* |
| Total tablet weight | 246 mg | 300 mg | 300 mg |

Figure 1B:
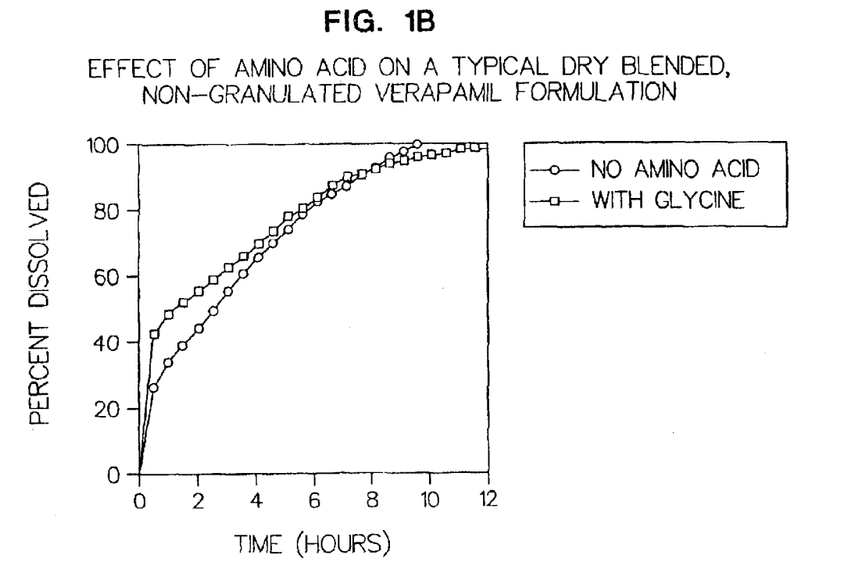

Example 1b (FIG. 1b) Illustrates the effect of adding amino acid to a dry blended, non granulated verapamil formulation, in which the verapamil HCl was not granulated, but blended with the two polymers prior to compression into a tablet.

| Component | Control Formulation | With Glycine |
|---|---|---|
| Verapamil HCl | 120 mg | 120 mg |
| Glycine | — | 54 mg |
| Guar Gum (G) | 54 mg | 54 mg |
| Guar Gum (U)* | 72 mg* | 72 mg* |
| Total tablet weight | 246 mg | 300 mg |

Example 2

Example 2a (FIG. 2a) Illustrates the effect of a combination of iso-leucine and glycine in a formulation containing nifedipine (a highly insoluble drug) versus a formulation containing no iso-leucine and glycine.

| Component | Test Formulation | Control |
|---|---|---|
| Nifedipine | 30 mg | 30 mg |
| Glycine | 24 mg | — |
| Iso-Leucine | 24 mg | — |
| Guar Gum (G) | 22 mg | 22 mg |
| Guar Gum (G)* | 22 mg* | 22 mg* |
| Total tablet weight | 122 mg | 74 mg |

Example 2b (FIG. 2b) Illustrates the effect of a combination of iso-leucine and glycine in a dry blended, non-granulated formulation containing nifedipine (a highly insoluble drug) versus a similar formulation containing no iso-leucine and glycine.

| Component | Test Formulation | Control |
|---|---|---|
| Nifedipine | 30 mg | 30 mg |
| Glycine | 24 mg | — |
| Iso-Leucine | 24 mg | — |
| Guar Gum (G) | 22 mg | 22 mg |
| Guar Gum (G)* | 22 mg* | 22 mg* |
| Total tablet weight | 122 mg | 74 mg |

Example 3

Example 3

Figure 3:
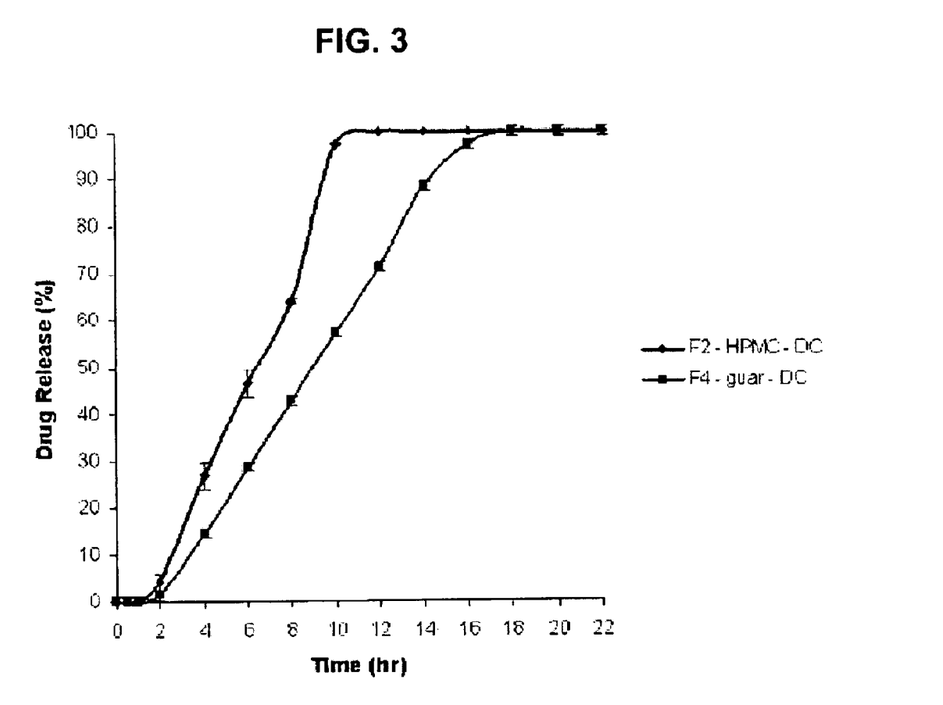
FIG. 3 illustrates the effects of amino acids on dissolution rates of dimenhydrinate formulations.

(FIG. 3) illustrates the effect of adding an intragranular amino acid to a typical dimenhydrinate formulation containing either HPMC or guar as an intragranular and extragranular polymer.

| Component | HPMC Formulation | Guar Formulation |
|---|---|---|
| Dimenhydrinate | 150 mg | 150 mg |
| Glycine | 50 mg | 50 mg |
| HPMC K4M | 30 mg | — |
| PEO WSRN 60K | 30 mg | — |
| MCC PH101 | 100 mg* | 100 mg* |
| Guar Gum (U)* | — | 100 mg* |
| Guar Gum (K) | — | 50 mg |
| Total tablet weight | 360 mg | 450 mg |

Example 4

Example 4

Figure 4:
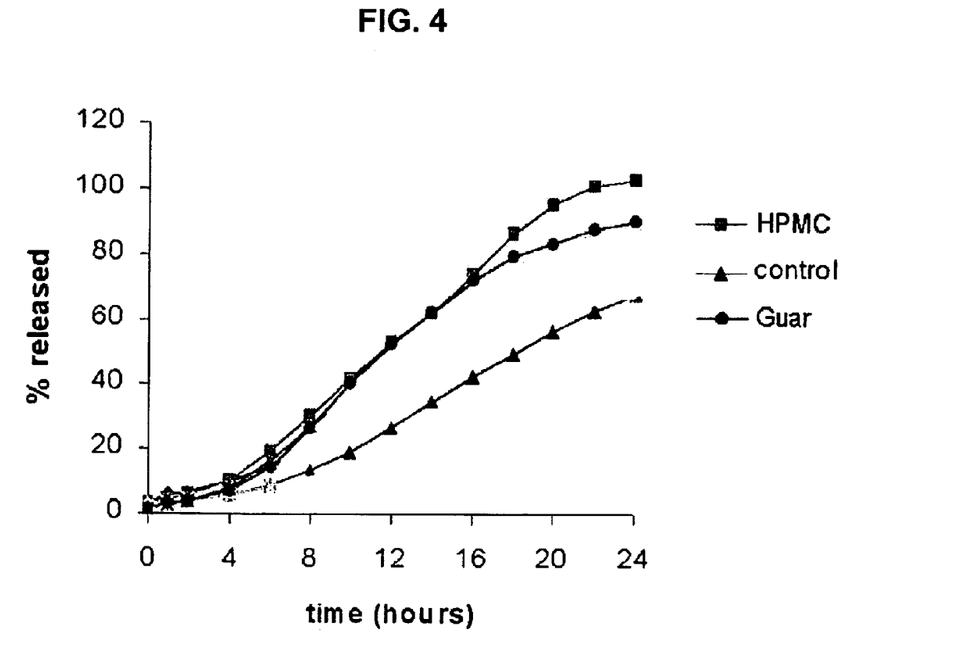
FIG. 4 illustrates the effects of amino acids on dissolution rates of ondansetron formulations.

(FIG. 4) illustrates the effect of adding an intragranular amino acid to a typical ondansetron formulation containing guar as an intragranular and extragranular polymer.

| Component | HPMC Formulation | Guar Formulation |
|---|---|---|
| Ondansetron HCl | 25 mg | 25 mg |
| Glycine | 25 mg | 25 mg |

-continued

| Component | HPMC Formulation | Guar Formulation |
|---|---|---|
| Citric Acid | 75 mg | 50 mg |
| HPMC K100M | 30 mg | — |
| PEO WSRN 301* | 150 mg* | — |
| MCC PH101* | 125 mg* | 132 mg* |
| Maltodextrin | — | 25 mg |
| Guar Gum (K) | — | 72 mg |
| Guar Gum (U)* | — | 96 mg* |
| Total tablet weight | 430 mg | 425 mg |

Example 5

Example 5

Figure 5:
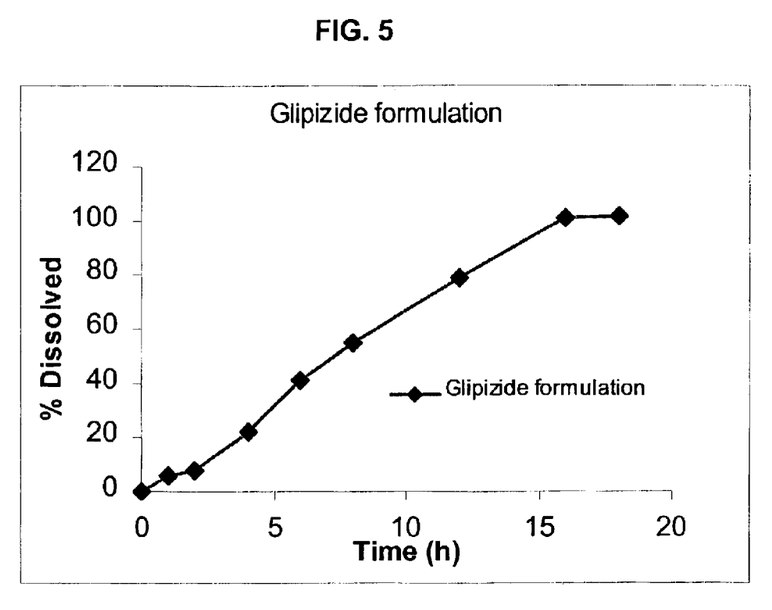
FIG. 5 illustrates the effects of amino acids on dissolution rates of glipizide formulations.

(FIG. 5) illustrates the effect of adding an intragranular amino acid to a typical glipizide formulation suitable for direct compression or granulation.

| Component | With Isoleucine |
|---|---|
| Glipizide | 11 mg |
| Glycine | 50 mg |
| Lactose | 50 mg |
| PEO WSRN 60K | 50 mg |
| PEO WSRN 60K* | 100 mg* |
| Lactose* | 50 mg* |
| Total tablet weight | 311 mg |

TABLE 1

| AMINO ACID | HYDROPHOBIC VALUE | CHARACTERIZATION |
|---|---|---|
| Isoleucine | 1.83 | Strongly Hydrophobic |
| Leucine | 1.80 | |
| Phenylalanine | 1.69 | |
| Tryptophan | 1.35 | |
| Valine | 1.32 | |
| Methionine | 1.10 | Moderately Hydrophobic |
| Proline | 0.84 | |
| Cysteine | 0.76 | |
| Tyrosine | 0.39 | Weakly Hydrophobic |
| Alanine | 0.35 | |
| Glycine | 0 | Neutral, Balanced |
| Threonine | −0.27 | Weakly Hydrophilic |
| Serine | −0.63 | |
| Histidine | −0.65 | |
| Glutamine | −0.93 | Moderately Hydrophilic |
| Asparagine | −0.99 | |
| Ornithine | −1.50 | Strongly Hydrophilic |
| Lysine | −1.54 | |
| Aspartic acid | −2.15 | |

What is claimed is:

1. An oral extended release dosage form comprising:
   (A) a plurality of granules comprising a pharmaceutically active compound, one or more amino acids selected from the group consisting of glycine, alanine, valine, leucine, iso-leucine, phenylalanine, proline, aspartic acid, glutamic acid, lysine, arginine, histidine, serine, threonine, cysteine, asparagine and glutamine, and an intragranular polymer; and,
   (B) a hydrophilic extragranular polymer in which said granules are dispersed, said extragranular polymer being more rapidly hydrating than said intragranular polymer, wherein:

the amino acid is selected for hydropathy characteristics depending on solubility characteristics of the active compound, and when said active compound is sparingly or more than sparingly soluble in water, said amino acid has a relatively equal balance between hydrophobic and hydrophilic components or is relatively more hydrophilic; and when said active compound is less than sparingly soluble in water, said amino acid is a combination of at least two amino acids, one of which is moderately or strongly hydrophobic, the other of which is relatively more hydrophilic.

2. The dosage form of claim 1, wherein the amount of amino acid in the dosage form is between 4% and 45% of the total dosage form weight.

3. The dosage form of claim 2, wherein the amount of amino acid in the dosage form is between 11% and 29% by weight of the total dosage form.

4. The dosage form of claim 1, wherein the pharmaceutically active compound is less than sparingly soluble in water and said amino acid is a combination of a hydrophobic amino acid and a weakly hydrophobic or a hydrophilic amino acid.

5. The oral extended release dosage form of claim 4, wherein the amino acid comprises glycine and a hydrophobic amino acid selected from iso-leucine, valine, and phenylalanine.

6. The dosage form of claim 1, wherein the pharmaceutically active compound is at least sparingly soluble in water or has a higher level of water solubility and said amino acid is has a relatively equal balance between hydrophilic and hydrophobic components or is relatively more strongly hydrophilic.

7. The oral extended release dosage form of claim 6, wherein said balanced amino acid comprises glycine.

8. The dosage form of claim 1, wherein said extragranular polymer comprises 4% to 47% of the total dosage form by weight.

9. The oral extended release dosage form of claim 1, wherein said pharmaceutically active compound release profile approximates a zero-order release profile over a period of 12 to 24 hours, without a significant initial burst effect.

10. The oral extended release dosage form of claim 9, wherein said tableted oral extended release dosage form achieves about 100% release of said pharmaceutically active compound over said period.

11. The oral extended release dosage form of claim 1, wherein the intragranular polymer comprises one or more of the following: polyethylene oxide, polyvinyl acetate, a galactomannan polysaccharide selected from the group consisting of hydroxypropyl guar, guar gum, locust bean gum, pectin, gum acacia, tragacanth and karaya gum, and a cellulose ether.

12. The oral extended release dosage form of claim 11, wherein the intragranular polymer comprises 4% to 45% of the total dosage form by weight.

13. The oral extended release dosage form of claim 1, wherein the extragranular polymer comprises one or more of the following: polyethylene oxide, a galactomannan polysaccharide selected from the group consisting of hydroxypropyl guar, guar gum, locust bean gum, pectin, gum acacia, gum tragacanth and karaya gum, and cellulose ethers.

14. The oral extended release dosage form of claim 13, wherein the extragranular polymer comprises 4% to 47% of the total dosage form by weight.

15. The oral extended release dosage form of claim 1, wherein the intragranular polymer is a galactomannan polysaccharide and the extragranular polymer is guar gum.

16. The oral extended release dosage form of claim 1, wherein said granule is blended with a hydrophobic coating material.

17. The oral extended release dosage form of claim 16, wherein said hydrophobic coating material is magnesium stearate.

18. The oral extended release dosage form claim 16, wherein said hydrophobic coating material is 1% to 3% of the total dosage form weight.

19. The oral extended release dosage form of claim 1, wherein said granule optionally contains conventional tableting additives selected from at least one of lactose, sucrose, maltose, maltodextrins, dextrins, starch, microcrystalline cellulose, fructose, sorbitol, di- and tri-calcium phosphate, starch, methylcellulose, hydroxy propyl cellulose, hydroxypropyl methyl cellulose, sodium carboxymethyl cellulose, polyvinyl pyrrolidone, gum acacia, tragacanth and sucrose.

20. The oral extended release dosage form of claim 1, wherein said pharmaceutically active compound is present in the amount of up to 75% of the total dosage form weight.

21. The oral extended release dosage form of claim 20, wherein the pharmaceutically active compound is selected from nifedipine, verapamil, ondansetron, dimenhydrinate, glipazide, metformin, paclitaxil, and pharmaceutically acceptable salts thereof, or combinations thereof.

22. The oral extended release dosage form of claim 1, wherein the plurality of granules comprises two or more pharmaceutically active compounds.

23. The oral extended release dosage form of claim 1, wherein one or more pharmaceutically active compounds are dispersed in said extragranular polymer.

24. The oral extended release dosage form of claim 1, wherein said extragranular polymer contains amino acids.

25. The oral extended release dosage form of claim 1, wherein said dosage form is coated with at least one of a polymer, a plasticizer, an opacifier, and a colourant.

26. A process of making a tableted oral extended release dosage form, the steps comprising:
   mixing a pharmaceutically effective amount of a pharmaceutically active compound, an intragranular polymer, and at least one amino acid to form a first mixture,
   forming said first mixture into granules,
   blending an extragranular polymer with said granules, and
   compressing the resulting blend into simple monolithic tablets, wherein said granules are dispersed in and substantially surrounded by said extragranular polymer, said extragranular polymer is more rapidly hydrating than said intragranular polymer, and wherein,
   the amino acid is selected for hydropathy characteristics depending on solubility characteristics of the active compound,
   when said active compound is at least sparingly soluble in water, said amino acid has a relatively equal balance between hydrophobic and hydrophilic components or is relatively more hydrophilic, and said active compound is verapamil, dimenhydrinate, metformin, pharmaceutically acceptable salts thereof, or combinations thereof
   when said active compound is less than sparingly soluble, said amino acid is a combination of at least two amino acids, one of which is strongly hydrophobic, the other of which is relatively more hydrophilic, and said active compound is nifedipine, ondansetron, glipazide, paclitaxil, pharmaceutally acceptable salts thereof, or combinations thereof.

* * * * *